(12) United States Patent
Jessop et al.

(10) Patent No.: US 7,776,010 B2
(45) Date of Patent: Aug. 17, 2010

(54) SYRINGE-IN-SYRINGE HOLLOW INNER BARREL/PLUNGER WITH INTEGRAL SEAL AND RUPTURABLE MEMBRANE AND RELATED KITS, SYSTEMS, AND METHODS

(75) Inventors: Neil Jessop, Sandy, UT (US); Bruce S. McLean, Sandy, UT (US); Jared Sheetz, Eagle Mountain, UT (US)

(73) Assignee: Ultradent Products, Inc., South Jordan, UT (US)

( * ) Notice: Subject to any disclaimer, the term of this patent is extended or adjusted under 35 U.S.C. 154(b) by 60 days.

(21) Appl. No.: 11/673,334

(22) Filed: Feb. 9, 2007

(65) Prior Publication Data

US 2007/0251839 A1 Nov. 1, 2007

Related U.S. Application Data

(63) Continuation-in-part of application No. 11/414,964, filed on May 1, 2006, now abandoned.

(51) Int. Cl.
*A61M 5/00* (2006.01)
(52) U.S. Cl. .............................. 604/87; 604/82; 604/85; 604/89; 604/90; 604/187
(58) Field of Classification Search ............. 604/82–85, 604/87–89, 91, 92, 187, 184, 231; 206/219
See application file for complete search history.

(56) References Cited

U.S. PATENT DOCUMENTS

| 2,869,543 | A | 1/1959 | Ratcliff et al. ................ 604/90 |
| 3,326,215 | A | 6/1967 | Sarnoff et al. ................. 604/90 |
| 3,348,546 | A | 10/1967 | Roberts et al. ................ 604/89 |
| 3,548,825 | A | 12/1970 | Shaw ........................... 604/91 |

(Continued)

FOREIGN PATENT DOCUMENTS

CA        1158063        12/1983

(Continued)

OTHER PUBLICATIONS

Office Action dated Jun. 23, 2008 cited in U.S. Appl. No. 11/537,807 (Copy Attached).

*Primary Examiner*—Kevin C Sirmons
*Assistant Examiner*—Bhisma Mehta
(74) *Attorney, Agent, or Firm*—Workman Nydegger

(57) ABSTRACT

A hollow inner plunger for use within a syringe-in-syringe mixing system for mixing a two-part dental composition. The hollow inner plunger includes a body having a continuous cylindrical wall defining an internal chamber for containing a first component. The body includes a proximal end and a distal end. A sealing plug and rupturable membrane are disposed at the distal end of the body, and the sealing plug and rupturable membrane are integrally formed together as a single piece (e.g., formed of a single piece of elastomeric material). An associated syringe-in-syringe mixing system includes a first plunger, the hollow inner plunger as described above, and a syringe barrel configured to contain a second component. When assembled, the first plunger is slidably disposed within the hollow inner plunger, and the hollow inner plunger is slidably disposed within the syringe barrel. The two components are initially separated by the rupturable membrane.

15 Claims, 6 Drawing Sheets

U.S. PATENT DOCUMENTS

| | | | | |
|---|---|---|---|---|
| 3,685,514 A | 8/1972 | Cheney | | 604/90 |
| 3,749,084 A | 7/1973 | Cucchiara | | 600/575 |
| 3,872,864 A | 3/1975 | Allen, Jr. | | 604/89 |
| 4,003,709 A | 1/1977 | Eaton et al. | | 422/86 |
| 4,229,813 A | 10/1980 | Lilly et al. | | 368/89 |
| 4,292,916 A | 10/1981 | Bradley et al. | | 116/205 |
| 4,313,440 A | 2/1982 | Ashley | | 604/191 |
| 4,412,836 A * | 11/1983 | Brignola | | 604/87 |
| 4,463,875 A | 8/1984 | Tepic | | |
| 4,464,174 A | 8/1984 | Ennis | | 604/90 |
| 4,476,866 A | 10/1984 | Chin | | 606/194 |
| 4,480,760 A | 11/1984 | Schonberger | | 215/230 |
| 4,693,706 A | 9/1987 | Ennis, III | | 604/87 |
| 4,743,229 A | 5/1988 | Chu | | |
| 4,987,849 A | 1/1991 | Sherman | | 116/206 |
| 5,032,178 A | 7/1991 | Cornell | | 106/35 |
| 5,045,283 A | 9/1991 | Patel | | 422/56 |
| 5,053,339 A | 10/1991 | Patel | | 436/2 |
| 5,057,434 A | 10/1991 | Prusik et al. | | |
| 5,228,573 A | 7/1993 | Pavelle et al. | | 206/459.1 |
| 5,317,987 A | 6/1994 | Muller et al. | | 116/206 |
| 5,354,285 A | 10/1994 | Mazurik et al. | | 604/191 |
| 5,395,325 A | 3/1995 | Moreno et al. | | 604/89 |
| 5,425,580 A | 6/1995 | Beller | | |
| 5,429,603 A * | 7/1995 | Morris | | 604/88 |
| 5,489,267 A | 2/1996 | Moreno et al. | | 604/89 |
| 5,509,530 A | 4/1996 | Wilson | | 206/220 |
| 5,534,562 A | 7/1996 | Jensen et al. | | 523/118 |
| 5,633,836 A | 5/1997 | Langer et al. | | 368/327 |
| 5,697,903 A | 12/1997 | Fischer | | |
| 5,725,499 A | 3/1998 | Silverstein et al. | | |
| 5,743,886 A | 4/1998 | Lynn et al. | | 604/191 |
| 5,756,356 A | 5/1998 | Yanagi et al. | | 436/7 |
| 5,802,015 A | 9/1998 | Rothschild et al. | | 368/10 |
| 5,839,592 A | 11/1998 | Hayes | | 215/230 |
| 5,876,372 A | 3/1999 | Grabenkort et al. | | 604/89 |
| 5,908,054 A | 6/1999 | Safabash et al. | | |
| 6,089,180 A | 7/2000 | Nichols, Jr. | | 116/309 |
| 6,234,190 B1 * | 5/2001 | Fischer et al. | | 137/68.23 |
| 6,331,076 B1 | 12/2001 | Coll | | 374/102 |
| 6,501,390 B1 | 12/2002 | Chainer et al. | | 340/870.16 |
| 6,540,072 B1 | 4/2003 | Fischer | | |
| 6,715,645 B2 | 4/2004 | Peuker et al. | | 222/129 |
| 6,743,194 B2 | 6/2004 | Sharon et al. | | 604/89 |
| 6,818,682 B2 | 11/2004 | Falsafi et al. | | 523/116 |
| 6,884,071 B2 | 4/2005 | Martin | | 433/90 |
| 2003/0186196 A1 | 10/2003 | Wang et al. | | 433/226 |
| 2004/0122359 A1 | 6/2004 | Wenz et al. | | |
| 2005/0023173 A1 | 2/2005 | Paoletti | | 206/459.5 |
| 2005/0177100 A1 | 8/2005 | Harper et al. | | 604/89 |

FOREIGN PATENT DOCUMENTS

| | | |
|---|---|---|
| DE | 10021313 | 11/2001 |
| JP | 9182760 | 7/1997 |
| JP | 05104534 | 4/2005 |
| WO | WO9209870 | 6/1992 |
| WO | WO2005050192 | 6/2005 |

* cited by examiner

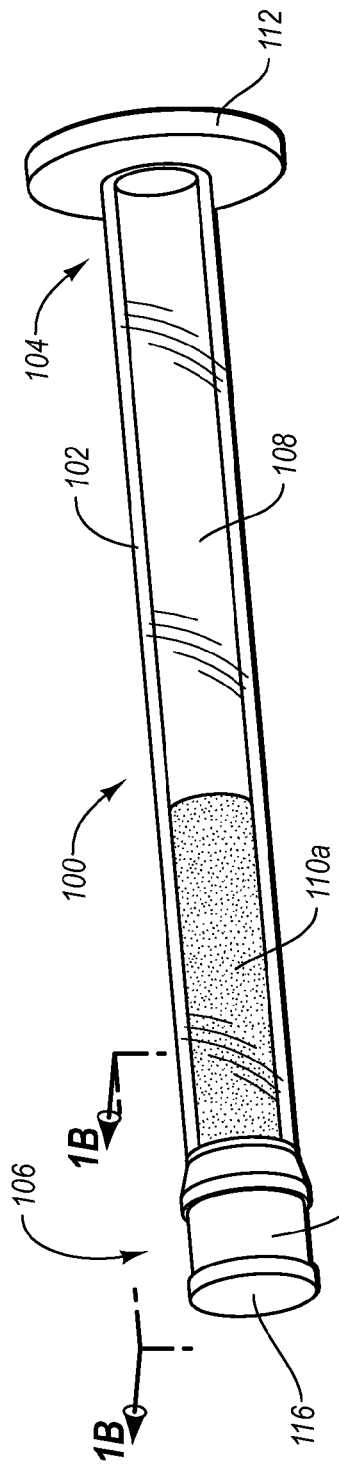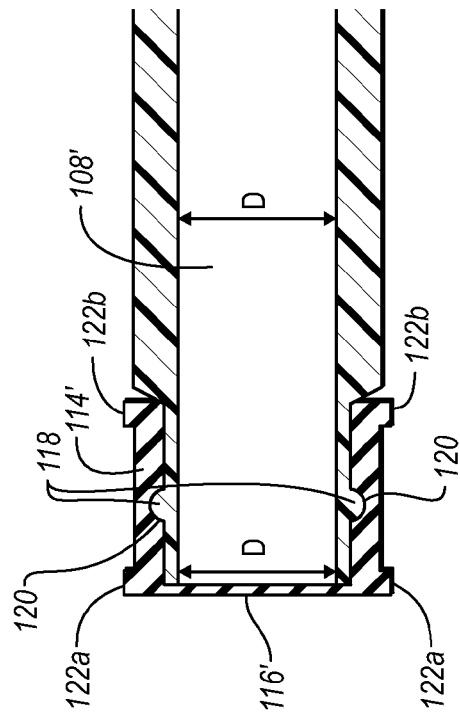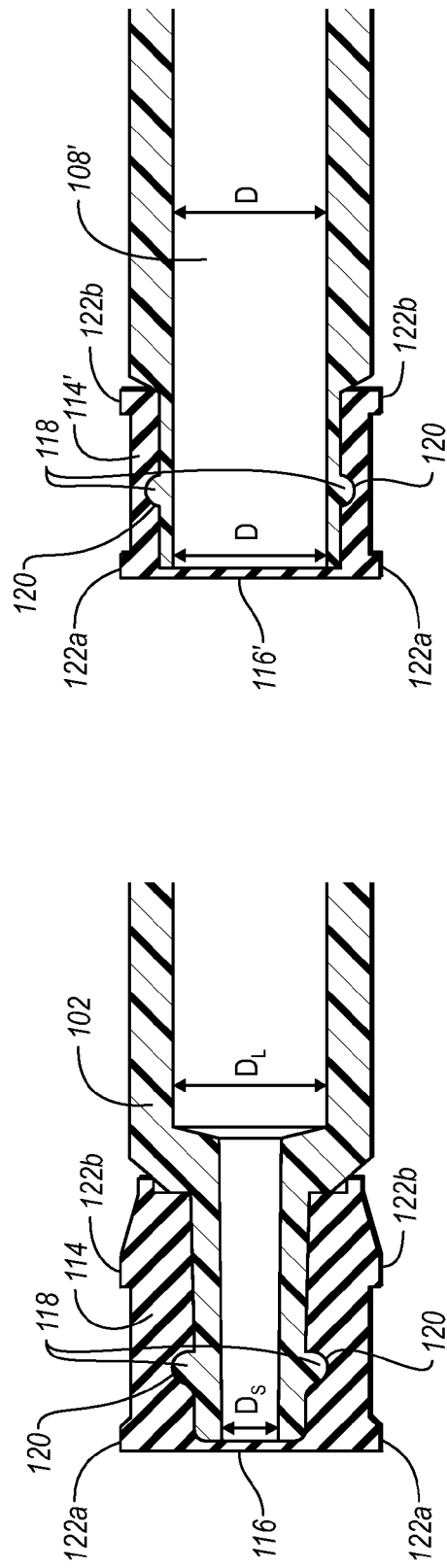

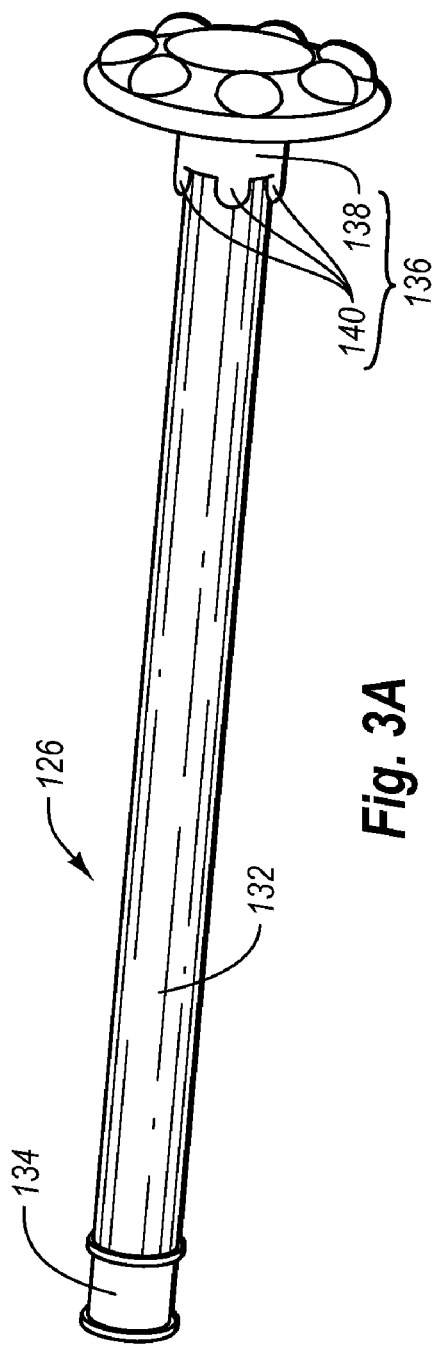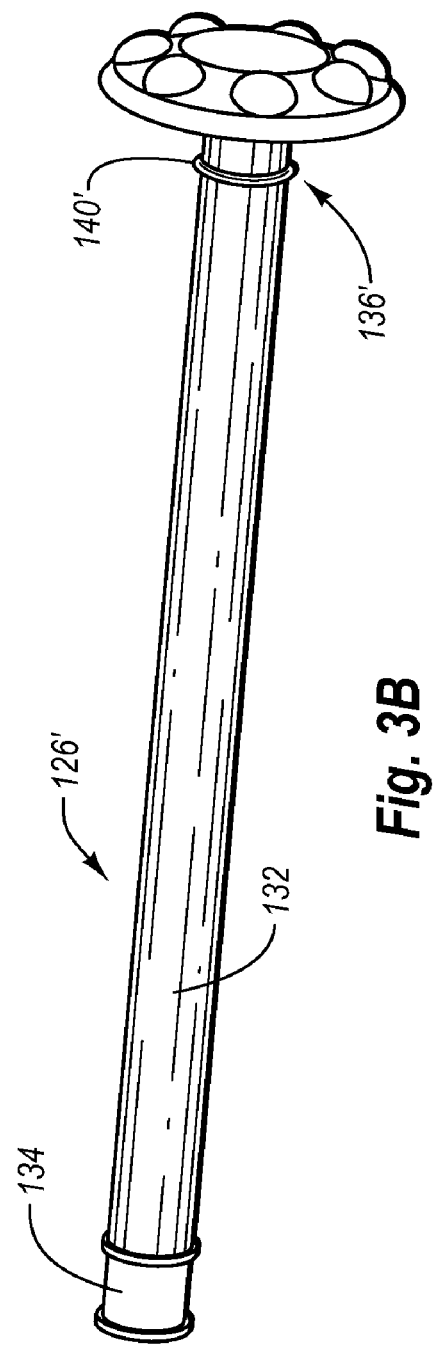

SYRINGE-IN-SYRINGE HOLLOW INNER BARREL/PLUNGER WITH INTEGRAL SEAL AND RUPTURABLE MEMBRANE AND RELATED KITS, SYSTEMS, AND METHODS

RELATED APPLICATIONS

The present application is a continuation-in-part of U.S. patent application Ser. No. 11/414,964, filed May 1, 2006, now abandoned, and entitled "TIME-INDICATING SYRINGE-IN-SYRINGE MIXING DEVICES AND RELATED METHODS FOR STORING AND DISPENSING TWO-PART DENTAL COMPOSITIONS, the disclosure of which is incorporated by reference in its entirety.

BACKGROUND OF THE INVENTION

1. The Field of the Invention

The present application is directed to devices and methods for mixing, storing and dispensing two-part dental compositions.

2. The Relevant Technology

Many chemical formulations are packaged in two initially separate parts, often known as A and B components. Separate storage of the A and B components is often necessary where the composition resulting from mixing is unstable over time. For example, a self-etching dental primer composition may be provided in two initially separate parts to prevent the acid component from slowly destabilizing the polymerizable resin component by hydrolyzing off the functional group(s) to which the backbone of the resin is chemically bonded. Although such destabilization may not occur immediately upon mixing, with many such compositions, it is often recommended that the composition be used up or discarded within a certain time period (e.g., 30, 60, or 90 days) after initial mixing.

Because such compositions are unstable once mixed, it is important to ensure that the two parts remain separated prior to mixing, so as to prevent premature mixing and destabilization. In addition, it is awkward and time consuming for the practitioner to have to measure each component from a larger container, and then mix them together prior to introducing the mixed composition into a storage and/or dispensing device. In light of the above, it would be an advantage to provide a syringe-in-syringe all in one mixing and dispensing system for use with a two-part composition that would provide a practitioner with pre-measured amounts of each component ready for mixing, and that would provide the user with an all in one device that could easily be activated to effect mixing, while also being used to store and later dispense the composition. It would be a further advantage if the all-in-one mixing and dispensing device reduced the possibility of premature mixing of the components, while also being inexpensive and easy to mass manufacture so as to be disposable after a single use.

BRIEF SUMMARY OF THE PREFERRED EMBODIMENTS

The present invention is directed to a hollow inner plunger for use within a syringe-in-syringe mixing system for mixing a two-part dental composition. The hollow inner plunger includes a body having a continuous cylindrical wall defining an internal chamber for containing a first component. The body includes a proximal end and a distal end. A sealing plug and rupturable membrane are disposed at the distal end of the body, and the sealing plug and rupturable membrane are integrally formed together as a single piece (e.g., formed of a single piece of elastomeric material).

Providing a sealing plug and rupturable membrane that are integral so as to comprise a single piece of material greatly simplifies the mass manufacture of the hollow inner plunger and a syringe-in-syringe mixing system of which it forms a part. The integral sealing plug and rupturable membrane provide a simple, low-cost way to ensure initial separation of the two-parts of a two-part dental composition within the syringe-in-syringe mixing system, while also minimizing and/or preventing contamination that may otherwise occur if the rupturable membrane were to comprise a separate part bonded to the distal end of the hollow inner plunger.

For example, any bonding adhesive used to bond a membrane may be contaminated or chemically attacked by one or both of the components separated by the rupturable membrane causing weakening or failure of the bond (e.g., during storage). Furthermore, where the composition is introduced into the chamber prior to bonding of the rupturable membrane, the composition may contaminate the wall or other surface to which the membrane is to be bonded, which may inhibit formation of a strong bond. In addition, any bonding adhesive may likewise contaminate or chemically react with one or both of the two components to be separated, which may render the mixed composition less effective or otherwise unsuitable for use. Therefore, providing an integral sealing plug and rupturable membrane not only reduces the number of parts and steps required in assembly, but also reduces the likelihood of contamination of the two-part composition or any bonding adhesive.

The hollow inner plunger may comprise part of an associated syringe-in-syringe mixing system for use in mixing and dispensing a two-part dental composition. Such a system includes a first plunger, the hollow inner plunger as described above, and a syringe barrel configured to contain a second component. When assembled, the first plunger is slidably disposed in sealing engagement within the hollow inner plunger, and the hollow inner plunger is slidably disposed in sealing engagement within the syringe barrel. The first component is initially stored within the chamber of the inner hollow plunger separate from the second component which is stored within the chamber of the syringe barrel. The two chambers are initially separated by the rupturable membrane.

In one embodiment, the internal chamber of the hollow inner plunger has a diameter at the distal end of the body that is less than a diameter of the chamber at the proximal end. Preferably, this narrowing of diameter occurs near the distal end of the body (e.g., adjacent to or near a proximal end of the integral sealing plug/rupturable membrane). Narrowing the diameter of the chamber significantly increases the pressure exerted by the first component against the rupturable membrane, which has been found to greatly aid in causing rupture of the membrane in such a way that results in jetting of the first component into the second component. The result of such jetting action is near instantaneous mixing of the two components, particularly for two relatively low viscosity liquids. As such, the internal diameter at the distal end is preferably not more than about 75% of the largest diameter of the chamber (e.g., the diameter at the proximal end), more preferably not more than about 50% of the largest diameter of the chamber (e.g., the diameter at the proximal end), and most preferably not more than about 35% of the largest diameter (e.g., the diameter at the proximal end). The inventors have found that a diameter at the distal end (i.e., adjacent the rupturable membrane) measuring about one-third that of the largest diameter of the chamber (e.g., the diameter from the proximal end to a location adjacent the sealing plug where the diameter is abruptly narrowed) results in catastrophic rupture of the membrane and jetting of substantially all of the first component through the rupturable membrane and into the second component to effect homogeneous mixing.

The actual thickness of the rupturable membrane depends on the strength and other physical properties of the selected material, along with the configuration of any reduction in diameter leading up to the proximal end of the body where the membrane is located. The rupturable membrane preferably has a thickness ranging from about 0.0005 inch to about 0.04 inch, more preferably from about 0.002 inch to about 0.025 inch, and most preferably from about 0.005 inch to about 0.015 inch. For example, it has been found that a thermoplastic elastomer material having a thickness from about 0.005 inch to about 0.010 inch is particularly preferred for the reasons described above when the diameter of the internal chamber is reduced adjacent the distal end to about one-third of its value at the proximal end.

These and other advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 1A is a perspective view of an exemplary hollow inner plunger including an integrally formed sealing plug and rupturable membrane;

FIG. 1B is a close up cross-sectional view of a distal end of the hollow inner plunger including the integral sealing plug and rupturable membrane of FIG. 1A;

FIG. 1C is a close up cross-sectional view of an alternative hollow inner plunger including an internal chamber of substantially constant diameter along its entire length;

FIG. 3A is a perspective view of an exemplary first plunger for use in a syringe-in-syringe mixing system, the first plunger including an exemplary locking mechanism to prevent pull-out of the first plunger once it has been fully inserted within the hollow inner plunger;

FIG. 3B is a perspective view of an alternative first plunger including an alternative locking mechanism;

DETAILED DESCRIPTION OF THE PREFERRED EMBODIMENTS

I. Introduction

Figure 2:
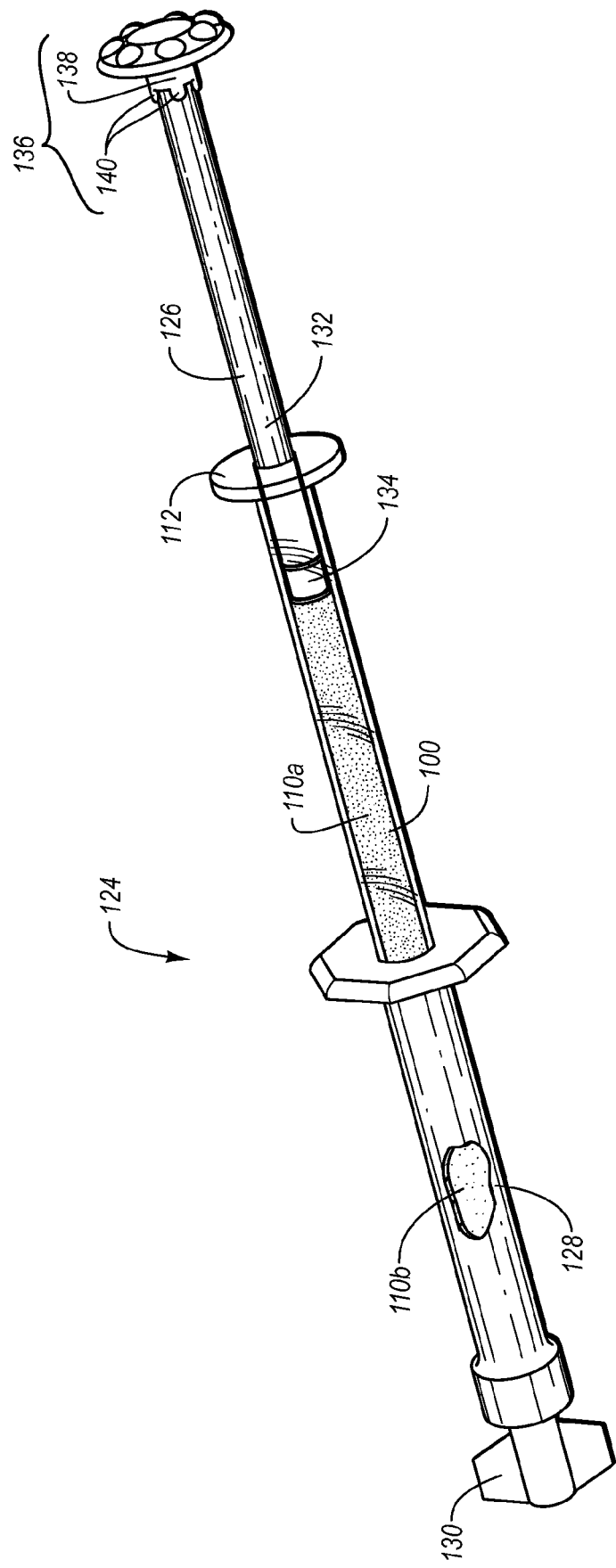
FIG. 2 is a perspective view of an exemplary syringe-in-syringe mixing system incorporating a hollow inner plunger according to the present invention.

In one aspect, the present invention is directed to a hollow inner plunger for use within a syringe-in-syringe mixing system for mixing a two-part dental composition. The hollow inner plunger includes a body having a continuous cylindrical wall defining an internal chamber for containing a first component. The body includes a proximal end and a distal end. A sealing plug and rupturable membrane are disposed at the distal end of the body, and the sealing plug and rupturable membrane are integrally formed together as a single piece (e.g., formed of a single piece of elastomeric material).

The hollow inner plunger may comprise part of an associated syringe-in-syringe mixing system for use in mixing and dispensing a two-part dental composition. Such a system includes a first plunger, the hollow inner plunger as described above, and a syringe barrel configured to contain a second component. When assembled, the first plunger is slidably disposed in sealing engagement within the hollow inner plunger, and the hollow inner plunger is slidably disposed in sealing engagement within the syringe barrel. The first component is initially stored within the chamber of the inner hollow plunger separate from the second component which is stored within the chamber of the syringe barrel. The two chambers are initially separated by the rupturable membrane.

II. Exemplary Hollow Inner Plungers

FIG. 1A is a perspective view of hollow inner plunger 100 having a body including a continuous cylindrical wall 102. The body and wall 102 include a proximal end 104 and an opposite distal end 106. The interior of wall 102 defines an internal chamber 108 configured to contain a first component 110a. A flange 112 is disposed at proximal end 104, while an integrally formed sealing plug and rupturable membrane 116 is disposed at distal end 106. Advantageously, and as shown in FIG. 1B, sealing plug 114 and membrane 116 are integrally formed as a single piece, for example, from an elastomeric material. Rupturable membrane portion 116 caps and seals off the opening of the distal end of hollow inner plunger 100 at the point where sealing plug 114 terminates at the opening, forming an uninterrupted surface across the entirety of the sealing plug portion and the membrane portion so as to contain first component 110a within chamber 108, keeping it separate from a second component until the user desires to effect mixing. Sealing plug 114 is disposed on the outside of body wall 102, extending laterally around the dispensing end of hollow inner plunger 100. Sealing plug 114 terminates at the opening of the dispensing end of hollow inner plunger 100 and is configured to plug within a syringe barrel (see FIG. 2) so as to seal the proximal end of the syringe barrel when the hollow inner plunger 100 is assembled into a syringe-in-syringe mixing system.

The distal portion of the body of hollow inner plunger 100 over which sealing plug 114 is fitted advantageously includes an outwardly extending annular ridge 118 near the dispensing end that prevents plug 114 from being separated from hollow inner plunger 100 during rupture of rupturable membrane 116. Sealing plug 114 includes a corresponding annular groove 120 configured to matingly engage ridge 118 so as to securely attach sealing plug and rupturable membrane 116 to the body of hollow inner plunger 100.

Sealing plug 114 and rupturable membrane 116 may advantageously be formed of an elastomeric material (e.g., a thermoset elastomer or thermoplastic elastomer), which advantageously provides an excellent seal against a syringe barrel while also providing a desired strength to rupturable membrane 116. Rupturable membrane 116 extends over the dispensing end of the hollow inner plunger at the point where sealing plug 114 terminates at the opening of the dispensing end, forming a flat, uninterrupted surface across the entirety of the sealing plug 114 and membrane 116 at which surface sealing plug 114 and membrane 116 both terminate such that membrane 116 seals off the distal end of hollow inner plunger 100, separating first component 110a from a second component 110b contained within a syringe barrel 128 (see FIG. 2) until the user intentionally ruptures membrane 116, causing first component 110a to be forced into syringe barrel 128, where the two components are mixed together.

Providing a sealing plug 114 and rupturable membrane 116 that are integral so as to comprise a single piece of material greatly simplifies the mass manufacture of the hollow inner plunger 100 and a syringe-in-syringe mixing system of which it forms a part. The integral sealing plug 114 and rupturable membrane 116 provide a simple, low-cost way to ensure initial separation of the two-parts of a two-part dental composition within a syringe-in-syringe mixing system, while also minimizing and/or preventing contamination that may otherwise occur if the rupturable membrane 116 and sealing plug 114 were to comprise two separate parts requiring bonding of each to the body or wall 102.

For example, any bonding adhesive used to bond a rupturable membrane to wall 102 (or any other structure) may be contaminated or chemically attacked by one or both of the components separated by the rupturable membrane (e.g., during storage). Such contamination or chemical reaction would likely lead to weakening and/or failure of the bond holding the membrane in place. Furthermore, where the composition is introduced into the chamber prior to bonding of the rupturable membrane, the composition may contaminate the wall or other surface to which the membrane is to be bonded, which may inhibit formation of a good bond.

In addition, any bonding adhesive may likewise contaminate or chemically react with one or both of the two components intended for separation within a syringe-in-syringe mixing system, which may render one component, both components, or the mixed composition less effective or otherwise unsuitable for use. Therefore, providing an integral sealing plug and rupturable membrane not only reduces the number of parts and steps required to assemble a hollow inner plunger and an associated syringe-in-syringe mixing system, but also reduces the likelihood of contamination of the two-part composition or any bonding adhesive, either of which could render the mixing system and/or composition useless.

FIGS. 1B and 1C illustrate cross-sectional views of alternative embodiments. FIG. 1B illustrates an example in which the inside diameter of the chamber 108 of hollow inner plunger 100 is reduced at the dispensing end adjacent to rupturable membrane 116, while FIG. 1C illustrates an alternative example in which the diameter D of the chamber 108' is not reduced, but is substantially constant along the length of the chamber 108' so that the diameter D adjacent membrane 116' and plug 114' is substantially the same as the diameter D elsewhere along chamber 108'.

FIG. 1B shows a preferred embodiment in which the internal chamber 108 of hollow inner plunger 100 has a diameter $D_S$ at distal end 106 of the body that is less than a diameter $D_L$ of the chamber at proximal end 104. As illustrated, preferably this narrowing of diameter occurs near the distal end 106 of the body. For example, in the illustrated embodiment, the narrowing of the chamber diameter occurs adjacent or near the proximal edge of the sealing plug 114. Reducing the outside diameter of the body wall 102 along this distal portion also provides space for the receipt of sealing plug 114 in a way that presents an overall outside diameter of the plunger 100 that is substantially constant along the entire length (i.e., between proximal end 104 adjacent flange 112 and distal end 106), with the exception of primary and secondary sealing surfaces 122a and 122b, respectively, which are configured to seal against the inside surface of a syringe barrel. Such an arrangement provides a tight fit of the inner plunger 100 within a syringe barrel (e.g., see FIG. 2), reducing any tendency of the inner plunger to wobble within the syringe barrel, which tendency may become particularly pronounced further away from the sealing surfaces 122a and 122b (e.g., near proximal end 104). In one embodiment sealing plug portion 114 fits cylindrically around the diametrically reduced portion of the distal end of hollow inner plunger 100 so as to terminate at the opening of the diametrically reduced distal end portion. Sealing plug 114 may have a diameter that is essentially the same as the diameter of the inner hollow plunger 100 leading up to the diametrically reduced portion. Sealing plug 114 may further include at least one sealing surface (e.g., surfaces 122a and 122b) to create a seal with the inside surface of a syringe barrel to prevent leakage of the components from the syringe barrel.

In addition, narrowing the diameter of chamber 108 significantly increases the pressure exerted by first component 110a against rupturable membrane 116, when force is selectively applied by a user to a plunger inserted within proximal end 104. Narrowing of diameter has been found to greatly aid in causing rupture of membrane 116 in such a way that results in jetting of first component 110a into second component 110b. The result of such jetting action is near instantaneous mixing of the two components, particularly for two relatively low viscosity liquids.

As such, the internal diameter $D_S$ at the distal end 106 is preferably not more than about 75% of the diameter $D_L$ at proximal end 104 and along the remainder of chamber 108, more preferably not more than about 50% of the diameter $D_L$, and most preferably not more than about 35% of the diameter $D_L$. The inventors have found that a diameter at the distal end (i.e., adjacent the rupturable membrane) measuring about one-third that of the largest diameter of the chamber (e.g., the diameter is substantially constant from the proximal end 104 to a location adjacent the sealing plug 114 where the diameter is abruptly narrowed) results in catastrophic rupture of the membrane and jetting of substantially all of the first component 110a through the rupturable membrane 116 and into the second component to effect homogeneous mixing.

The actual thickness of rupturable membrane portion 116 depends on the strength and other physical properties of the selected material, along with the configuration of any reduction in diameter leading up to the proximal end of the body where the membrane is located. The rupturable membrane portion preferably has a thickness ranging from about 0.0005 inch to about 0.04 inch, more preferably from about 0.002 inch to about 0.025 inch, and most preferably from about 0.005 inch to about 0.015 inch. For example, it has been found that a rupturable membrane formed of a thermoplastic elastomer material having a thickness from about 0.005 inch to about 0.010 inch is particularly preferred for the reasons described above when the diameter $D_S$ of the internal chamber 108 is reduced adjacent the distal end 106 to about one-third of its value at the proximal end 104.

III. Exemplary Syringe-In-Syringe Mixing Systems

FIG. 2 illustrates an exemplary syringe-in-syringe mixing system 124. System 124 includes a first plunger 126, a hollow inner plunger 100, and a syringe barrel 128 with a cap 130 at a distal end of syringe barrel 128 (a plug fitting inside the distal end of barrel 128 could equivalently be used). First plunger 126 is slidably disposed within hollow inner plunger 100, which is slidably disposed within syringe barrel 128. As illustrated, hollow inner plunger 100 contains a first component 110a, and syringe barrel 128 contains a second component 110b. First plunger 126 includes an elongate stem 132 and an associated sealing plug 134 at a distal end of stem 132.

As perhaps best seen in FIG. 3A, a locking mechanism 136 may advantageously be included near a proximal end of first plunger 126 to prevent withdrawal of first plunger 126 from inner plunger 100 once inserted. Such a locking mechanism is helpful as once the membrane is ruptured, the device cannot be reused for mixing two components, although it can be used to dispense the mixed composition until all has been dispensed. Locking first plunger within inner plunger 100 allows the dispensing device to operate as a syringe comprising a barrel and plunger, which simplifies dispensing by the user while also preventing slideout of the first plunger, which could result in loss, contamination or waste of the mixed composition. Illustrated locking mechanism 136 comprises a circumferentially extending portion of enlarged diameter 138 (relative to the remainder of stem 132), with a plurality of longitudinally extending interlock ribs 140. In use, interlock ribs 140 are inserted into hollow inner plunger 100, where the ribs 140 bias against the inside wall 102 of hollow inner plunger 100. The system is configured such that when first plunger 126 is fully inserted into hollow inner plunger 100, circumferentially extending portion 138 rests within flange 112 of hollow inner plunger 100, while interlock ribs 140 extend distally into hollow inner plunger 100, past flange 112. Because flange 112 provides increased barrel strength relative to the remainder of hollow inner plunger 100, little or no deformation occurs to the inside wall of hollow inner plunger 100 on account of portion 138, but deformation is caused by ribs 140, resulting in associated indentations being formed into the inside wall 102 of hollow plunger 100 distal to flange 112, preventing, or at least inhibiting, later removal of first plunger 126 from hollow inner plunger 100 (e.g., see FIG. 4B).

FIG. 3B illustrates an alternative first plunger 126' including a cylindrical elongate stem 132, and a sealing plug 134. The principle difference between the first plunger 126' and first plunger 126 of FIG. 3A and FIG. 2 is that first plunger 126' includes an alternative locking mechanism 136' comprising an annular interlock ring 140' rather than the enlarged diameter portion 138 and plurality of interlock ribs 140 of the embodiment of FIG. 3A. Similar to interlock ribs 140, annular interlock ring 140' causes the formation of an indentation or groove within the inside wall 102 of hollow inner plunger 100. Annular interlock ring 140' resides in the formed groove, preventing, or at least inhibiting, pull out of first plunger 126 once fully inserted into hollow inner plunger 100. Other locking mechanisms (e.g., an interference fit of the first plunger into the hollow inner plunger) may alternatively be used.

According to one method, a pre-measured, pre-filled syringe-in-syringe mixing system (as shown in FIG. 2) may be manufactured by first inserting first plunger 126 into hollow inner plunger 100 so that first plunger 126 is slidably received within hollow inner plunger 100. Sealing plug 134 of first plunger 126 seals the proximal end of hollow inner plunger. First component 110a may then be introduced into internal chamber 108 of hollow inner plunger 100. Integrally formed rupturable membrane 116 and sealing plug 114 may then be placed over distal end 106 of hollow inner plunger 100, effectively sealing first component 110a within chamber 108. Next, hollow inner plunger 100 may be inserted into syringe barrel 128 so that hollow inner plunger 100 is slidably received therein. Primary and secondary sealing surfaces 122a and 122b, respectively, form a seal to prevent passage of any fluid around seal 114, while membrane 116 forms a seal to prevent passage of any fluid through seal 114 until the membrane is intentionally ruptured by the user. Second component 110b may then be introduced into syringe barrel 128 through the distal end of the barrel. Cap 130 may finally be placed over the distal end of barrel 128 so seal the distal end. Assembly in such a manner prevents or at least minimizes the formation and entrapment of air bubbles within the chamber of the inner plunger 100 and/or the syringe barrel 128, and is thus currently preferred.

III. Exemplary Method of Use

Figure 4A:
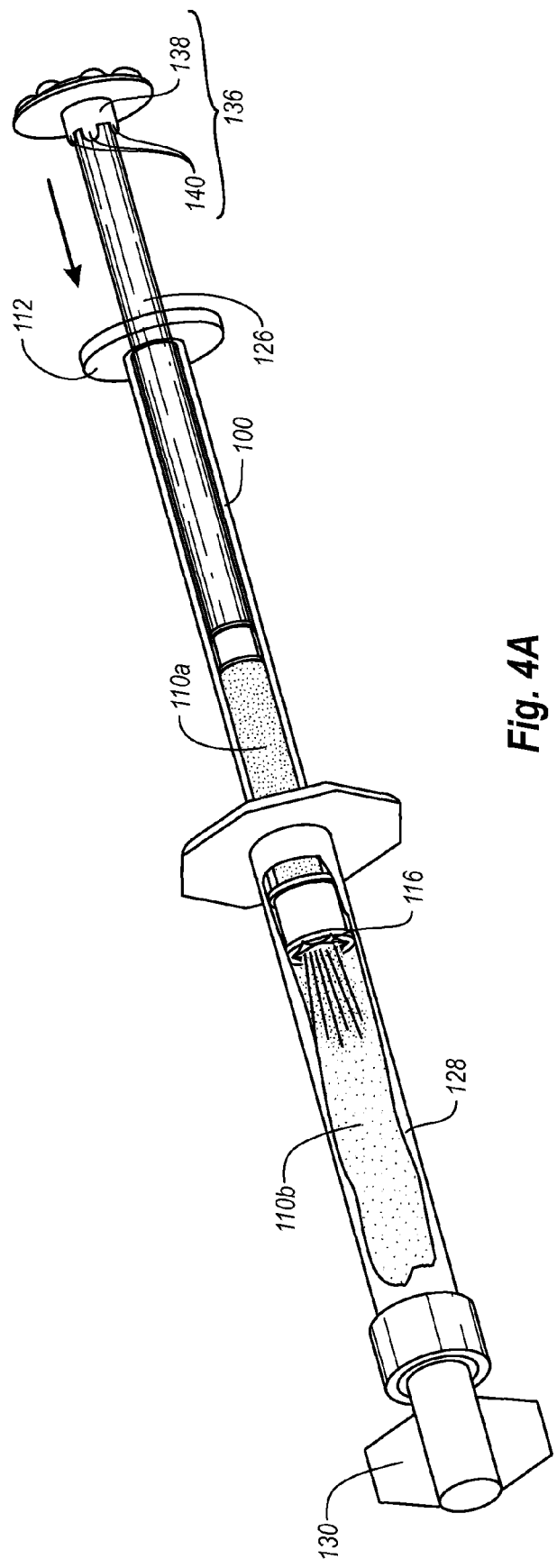
FIG. 4A illustrates the first plunger being pressed into the hollow inner plunger so as to cause the rupturable membrane at the distal end of the hollow inner plunger to break, resulting in jet mixing of the first component into the second component.

FIG. 4A illustrates an exemplary syringe-in-syringe mixing system 124. When it is desired to effect mixing of the two-part composition, the user may press first plunger 126 to cause plunger 126 to slide into hollow inner plunger 100 so as to compress first component 110a. Once a sufficient force is applied, pressure against the rupturable membrane portion causes rupture of membrane 116. Rupturable membrane 116 breaks causing first component 110a to be expressed under pressure from hollow inner plunger 100, introducing first component 110a into syringe barrel 128 where it contacts and/or mixes with second component 110b.

The force of such rupture and jetting of the first component 110a into the second component 110b is sufficient to effect homogeneous mixing, such that no additional mixing (e.g., by shaking) is required, particularly where both components are low viscosity liquids. Although preferred for use with liquid-liquid systems, first and second components 110a and 110b may each be a liquid, or one may be a solid powder, as dictated by the characteristics of the two-part composition to be mixed. The syringe-in-syringe mixer is particularly well suited for mixing together two relatively low viscosity liquids (e.g., less than about 100 centipoise, more preferably less than about 10 centipoise, and most preferably less than about 3 centipoise), because of the ability of the system to cause one component to be forcefully ejected into the other component so as to effect mixing without any additional effort (e.g., shaking is not necessary). One contemplated relatively low viscosity liquid-liquid two-part composition is a two-part self etching dental primer composition described in U.S. patent application Ser. No. 11/261,171, filed Oct. 28, 2005, and entitled SELF-ETCHING DENTAL PRIMER COMPOSITIONS AND METHODS AND SYSTEMS UTILIZING SUCH COMPOSITIONS, herein incorporated by reference.

Although particularly well suited for use with lower viscosity liquids, the system may also be used with higher viscosity liquids (e.g., up to about 1000 centipoise or even up to about 3500 centipoise) or a liquid-solid powder two-part composition, although when used for mixing such two-part compositions further mixing beyond that provided by the rupture of the membrane and turbulent jetting of one component into the other may be necessary. For example, it may be helpful when mixing such a composition to remove cap 130 and couple the system to another syringe so as to allow syringe-to-syringe mixing of the composition.

In other words, the rupturable membrane 116 is configured to only pass first component 110a for mixing with second component 110b under a pressure sufficiently high to cause jetting of the first component into the second component (e.g., so as to create turbulence sufficient to mix the two components together). Cap 130 may include a check-valve or other vent (not shown) that permits air or other gas within barrel 128 to be expelled as first component 110a is expressed into barrel 128. Any check-valve known in the art can be used or modified to attach to barrel 128.

Figure 4B:
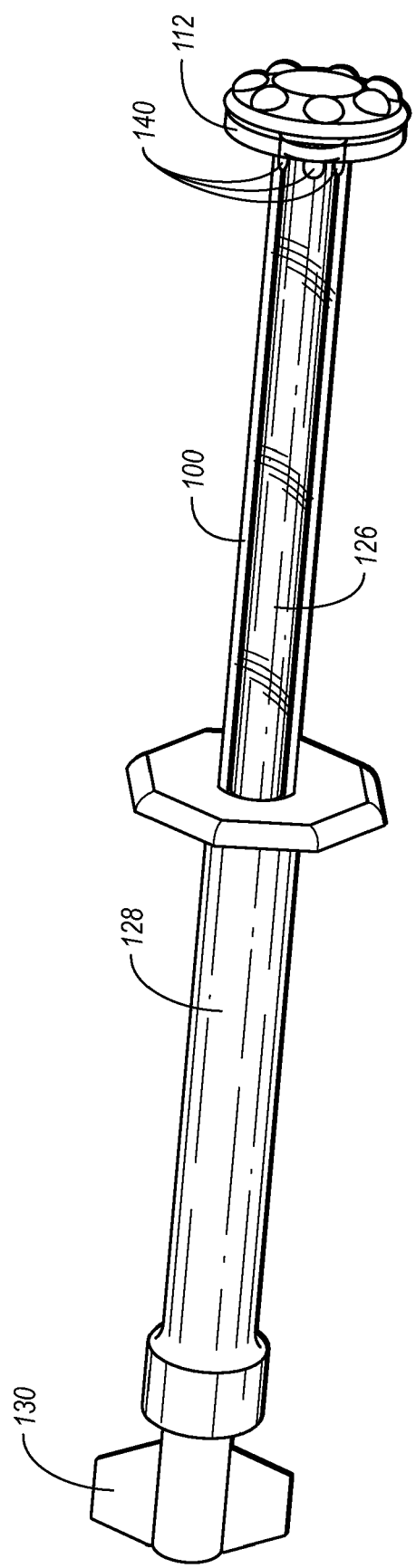
FIG. 4B illustrates the first plunger in a locked configuration relative to the hollow inner plunger so as to prevent pull-out of the first plunger from the hollow inner plunger.

The system may advantageously be configured such that a force required to rupture membrane 116 is approximately equal to a force required to insert and lock locking mechanism 136 (i.e., enlarged diameter portion 138 and interlocking ribs 140) of the cylindrical elongate stem 132 into hollow inner plunger 100, although it is not required. Such a configuration provides a smooth and continuous movement and feel during use of the system as first plunger 126 is pressed into hollow inner plunger 100, rupturing membrane 116 and locking first plunger 126 into hollow inner plunger 100, all within a single movement. FIG. 4B illustrates the system once first plunger 126 has been fully inserted into hollow inner plunger 100. In this configuration, first plunger 126 is locked into hollow inner plunger 100.

In the locked configuration as shown, it is difficult, if not impossible, to withdraw first plunger 126 from hollow inner plunger 100 without destroying the system. Enlarged diameter portion 138 is disposed within the center of flange 112, while ribs 140 extend distally from flange 112 further into hollow inner plunger 100. Because flange 112 has increased barrel strength relative to the area of hollow inner plunger 100 immediately distal to flange 112, the inside wall surface 102 of hollow inner plunger will be deformed by ribs 140 so as to form a depression into the portion of the contacted inside wall 102. At the same time, the inside wall surface 102 of hollow inner plunger 100 directly under flange 112 will be deformed only slightly if at all because of the increased barrel strength of the flange region 112 compared to the region contacted by ribs 140. In other words, ribs 140 create an interlock with the inside surface of hollow inner plunger 100, preventing, or at least inhibiting, subsequent withdrawal of first plunger 126 from hollow inner plunger 100.

Figure 4C:
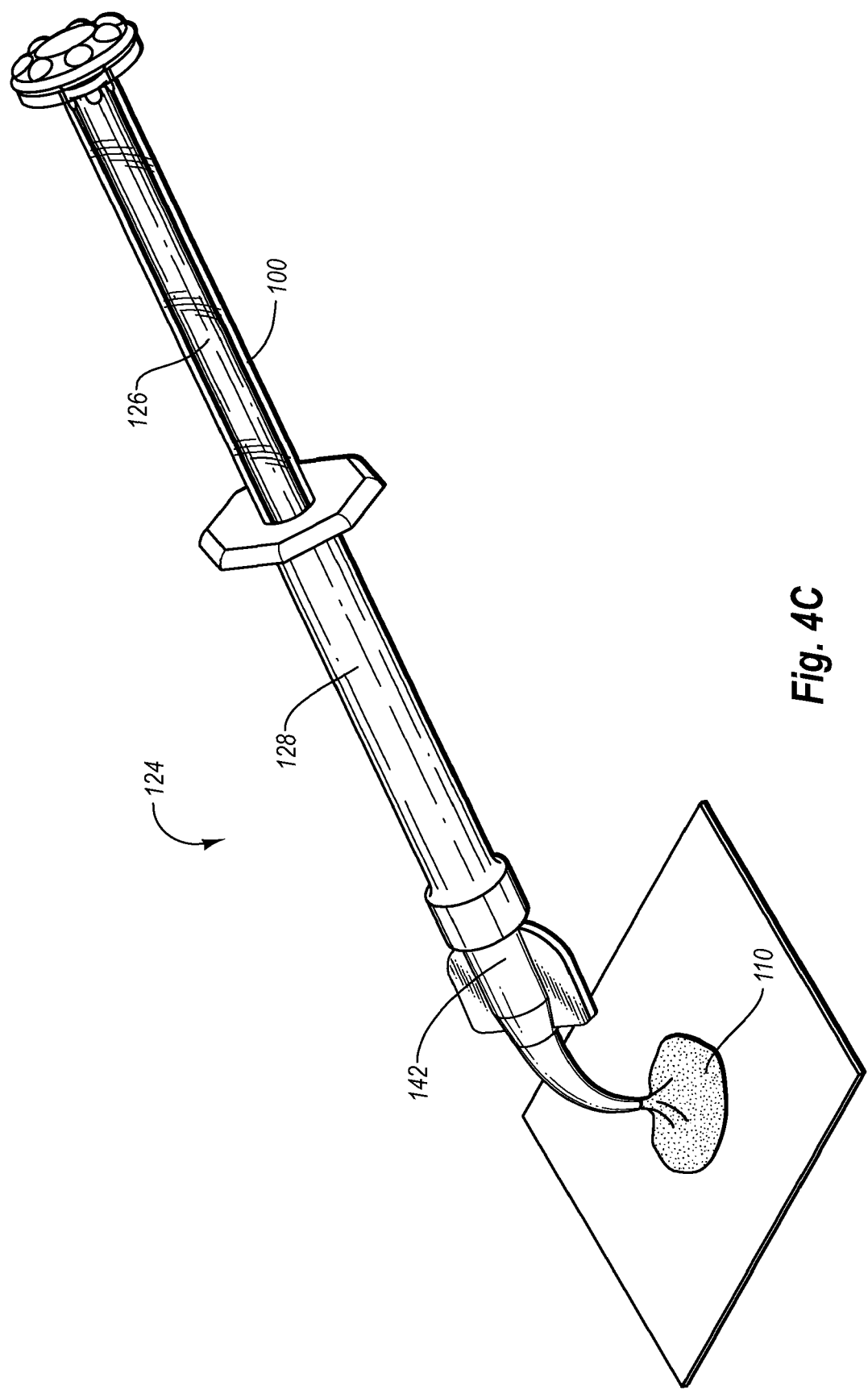
FIG. 4C illustrates dispensing of a portion of the mixed two-part composition onto a pad for subsequent application to a desired surface.

FIG. 4C illustrates the system 124 with a dispensing tip 142 coupled at a distal end of barrel 128 so as to allow the user to dispense the mixed two-part composition 110. As locked, hollow inner plunger 100 and first plunger 126 may together be used to function as a second plunger for syringe barrel 128. As illustrated, composition 110 may be dispensed onto a pad for subsequent application (e.g., with a brush tool). Alternatively composition 110 may be dispensed directly onto a tooth or other surface, depending on the preference of the user.

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

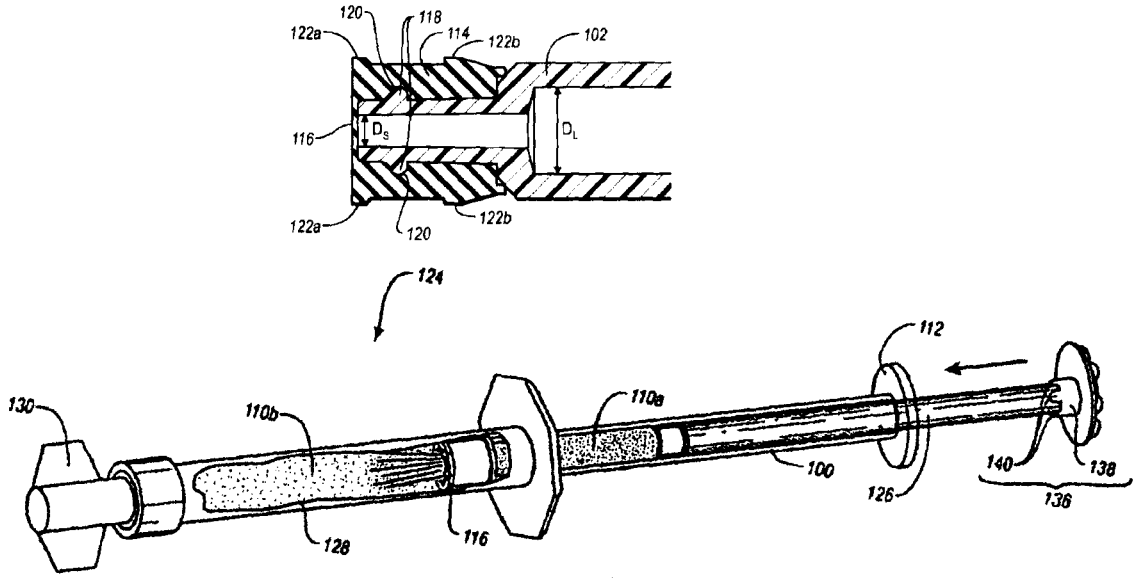

What is claimed is:

1. A syringe-in-syringe mixing system for use in mixing a two-part dental composition comprising:

a first component contained in an inner hollow plunger with a first plunger slidable within the inner hollow plunger;

a second component contained in a syringe barrel, the inner hollow plunger being disposed within the syringe barrel so that after the first plunger slides into and is locked within the inner hollow plunger, the inner hollow plunger and first plunger may together be used to function as a second plunger for the syringe barrel;

the inner hollow plunger including an integrally formed sealing plug and rupturable membrane disposed over a dispensing end of the inner hollow plunger;

the integrally formed sealing plug and rupturable membrane including a sealing plug portion laterally disposed around said dispensing end of the inner hollow plunger so as to terminate at an opening of the dispensing end and so as to sealingly engage against the interior of the syringe barrel; and the integrally formed sealing plug and rupturable membrane comprising a rupturable membrane portion that extends over the dispensing end of the inner hollow plunger at the point where the sealing plug portion terminates at said opening of the dispensing end, forming an uninterrupted surface across the entirety of the sealing plug portion and the membrane portion at which the sealing plug and membrane portions both terminate, and wherein by sliding the first plunger into the inner hollow plunger when expelling the first component, pressure against the membrane portion causes rupture of the membrane portion, introducing the first component into the syringe barrel so that the first component contacts the second component.

2. A system as recited in claim 1, wherein the inner hollow plunger has an inside diameter at said dispensing end adjacent the membrane portion that is less than an inside diameter of the inner hollow plunger at a proximal end of the inner hollow plunger.

3. A system as recited in claim 1, wherein the inner hollow plunger has an inside diameter at said dispensing end adjacent the membrane portion that is not more than about 75% of the inside diameter of the inner hollow plunger at a proximal end of the inner hollow plunger, in order to increase pressure exerted on the membrane portion when expelling contents of the inner hollow plunger by pushing the first plunger into the inner hollow plunger.

4. A system as recited in claim 1, wherein the inner hollow plunger has an inside diameter at said dispensing end adjacent the membrane portion that is not more than about 50% of the inside diameter of the inner hollow plunger at a proximal end of the inner hollow plunger, in order to increase pressure exerted on the membrane portion when expelling contents of the inner hollow plunger by pushing the first plunger into the inner hollow plunger.

5. A system as recited in claim 1, wherein the inner hollow plunger has an inside diameter at said dispensing end adjacent the membrane portion that is not more than about 35% of the inside diameter of the inner hollow plunger at a proximal end of the inner hollow plunger, in order to increase pressure exerted on the membrane portion when expelling contents of the inner hollow plunger by pushing the first plunger into the inner hollow plunger.

6. A system as recited in claim 1, wherein the integrally formed sealing plug and rupturable membrane comprise an elastomeric material.

7. A system as recited in claim 1, wherein the integrally formed sealing plug and rupturable membrane comprise a thermoplastic elastomer or a thermoset elastomer.

8. A system as recited in claim 1, wherein the membrane portion has a thickness between about 0.0005 inch and about 0.04 inch.

9. A system as recited in claim 1, wherein the membrane portion has a thickness between about 0.002 inch and about 0.025 inch.

10. A system as recited in claim 1, wherein the membrane portion has a thickness between about 0.005 inch and about 0.015 inch.

11. A system as recited in claim 1, wherein the inner hollow plunger further includes an outwardly extending annular ridge disposed near the dispensing end of the inner hollow plunger, the sealing plug portion of the integrally formed sealing plug and rupturable membrane further including a corresponding annular groove configured to matingly engage the annular ridge so as to attach the sealing plug and rupturable membrane to the inner hollow plunger.

12. A syringe-in-syringe mixing system for use in mixing a two-part dental composition comprising:
  a first component pre-packaged in an inner hollow plunger having a first plunger slidable into the inner hollow plunger to expel the first component from the inner hollow plunger, the inner hollow plunger terminating in a diametrically reduced distal end portion having an opening, the first plunger comprising a locking mechanism to prevent withdrawal of the first plunger from the inner hollow plunger once the first component has been expelled;
  a second component pre-packaged in a barrel of a syringe, the inner hollow plunger being disposed within the syringe barrel so that after the first plunger is inserted and locked by the locking mechanism into the inner hollow plunger when expelling the contents of the inner hollow plunger, thereafter the inner hollow plunger and first plunger, as locked, serve to function together as a second plunger within the syringe barrel;
  an integrally formed sealing plug and rupturable membrane that both caps and seals said distal end of the inner hollow plunger, said integrally formed sealing plug and rupturable membrane comprising,
    a sealing plug portion which fits cylindrically around said diametrically reduced portion of the distal end of the inner hollow plunger so as to terminate at said opening of the diametrically reduced distal end portion, said sealing plug portion having a diameter that is essentially the same as the diameter of the inner hollow plunger leading up to said diametrically reduced portion, and the sealing plug portion also comprising at least one sealing surface configured to create a seal with the inside surface of the barrel of the syringe to prevent leakage of the first and second components from the barrel of the syringe; and
    a rupturable membrane portion which caps said opening of the distal end of the inner hollow plunger at the point where said sealing plug portion terminates at said opening, forming an uninterrupted surface across substantially the entirety of the sealing plug portion and the membrane portion, said rupturable membrane portion being formed as an integral part which joins the sealing plug portion, and wherein by sliding the first plunger into the inner hollow plunger when expelling the first component, pressure against the rupturable membrane portion causes rupture of the membrane, introducing the first component into the syringe barrel so that the first component contacts the second component.

13. A system as recited in claim 12, wherein the rupturable membrane portion has a thickness between about 0.002 inch and about 0.025 inch.

14. A system as recited in claim 12, wherein the rupturable membrane portion has a thickness between about 0.005 inch and about 0.015 inch.

15. A system as recited in claim 12, wherein the inner hollow plunger has an inside diameter at said distal end that is not more than about 75% of the inside diameter of the rest of the inner hollow plunger.

\* \* \* \* \*

UNITED STATES PATENT AND TRADEMARK OFFICE
CERTIFICATE OF CORRECTION

| | | |
|---|---|---|
| PATENT NO. | : 7,776,010 B2 | |
| APPLICATION NO. | : 11/673334 | |
| DATED | : August 17, 2010 | |
| INVENTOR(S) | : Jessop et al. | |

It is certified that error appears in the above-identified patent and that said Letters Patent is hereby corrected as shown below:

Title page should be deleted and substitute therefor the attached title page.

Column 4
Line 38, change "sealing plug" to --sealing plug 114--
Line 39, change "is" to --are--

Column 7
Line 60, change "first plunger 126" to --first plunger 126'--

Column 8
Line 17, after "so" insert --as to--

Signed and Sealed this
First Day of March, 2011

David J. Kappos
*Director of the United States Patent and Trademark Office*

CERTIFICATE OF CORRECTION (continued)

(12) United States Patent
Jessop et al.

(10) Patent No.: US 7,776,010 B2
(45) Date of Patent: Aug. 17, 2010

(54) SYRINGE-IN-SYRINGE HOLLOW INNER BARREL/PLUNGER WITH INTEGRAL SEAL AND RUPTURABLE MEMBRANE AND RELATED KITS, SYSTEMS, AND METHODS

(75) Inventors: Neil Jessop, Sandy, UT (US); Bruce S. McLean, Sandy, UT (US); Jared Sheetz, Eagle Mountain, UT (US)

(73) Assignee: Ultradent Products, Inc., South Jordan, UT (US)

( * ) Notice: Subject to any disclaimer, the term of this patent is extended or adjusted under 35 U.S.C. 154(b) by 60 days.

(21) Appl. No.: 11/673,334

(22) Filed: Feb. 9, 2007

(65) Prior Publication Data

US 2007/0251839 A1 Nov. 1, 2007

Related U.S. Application Data

(63) Continuation-in-part of application No. 11/414,964, filed on May 1, 2006, now abandoned.

(51) Int. Cl.
*A61M 5/00* (2006.01)

(52) U.S. Cl. .................. 604/87; 604/82; 604/85; 604/89; 604/90; 604/187

(58) Field of Classification Search ............ 604/82–85, 604/87–89, 91, 92, 187, 184, 231; 206/219
See application file for complete search history.

(56) References Cited

U.S. PATENT DOCUMENTS 2,869,543 A 1/1959 Ratcliff et al. .............. 604/90

3,548,825 A 12/1970 Shaw ......................... 604/91

(Continued)

FOREIGN PATENT DOCUMENTS

CA 1158063 12/1983

(Continued)

OTHER PUBLICATIONS

Office Action dated Jun. 23, 2008 cited in U.S. Appl. No. 11/537,807 (Copy Attached).

*Primary Examiner*—Kevin C Sirmons
*Assistant Examiner*—Bhisma Mehta
(74) *Attorney, Agent, or Firm*—Workman Nydegger

(57) ABSTRACT

A hollow inner plunger for use within a syringe-in-syringe mixing system for mixing a two-part dental composition. The hollow inner plunger includes a body having a continuous cylindrical wall defining an internal chamber for containing a first component. The body includes a proximal end and a distal end. A sealing plug and rupturable membrane are disposed at the distal end of the body, and the sealing plug and rupturable membrane are integrally formed together as a single piece (e.g., formed of a single piece of elastomeric material). An associated syringe-in-syringe mixing system includes a first plunger, the hollow inner plunger as described above, and a syringe barrel configured to contain a second component. When assembled, the first plunger is slidably disposed within the hollow inner plunger, and the hollow inner plunger is slidably disposed within the syringe barrel. The two components are initially separated by the rupturable membrane.